United States Patent [19]

Funke

[11] 3,937,226

[45] Feb. 10, 1976

[54] ARRHYTHMIA PREVENTION APPARATUS
[75] Inventor: Herman D. Funke, Bonn, Germany
[73] Assignee: Medtronic, Inc., Minneapolis, Minn.
[22] Filed: July 10, 1974
[21] Appl. No.: 487,241

[52] U.S. Cl. .............................................. 128/419 D
[51] Int. Cl.² ............................................. A61N 1/36
[58] Field of Search ..... 128/2.06 A, 2.06 F, 2.06 R, 128/419 DC, 419 PE, 419 PG, 419 R, 421, 422, 2.1 B

[56] References Cited
UNITED STATES PATENTS

| | | | |
|---|---|---|---|
| 3,138,151 | 6/1964 | Chapman et al. ............... | 128/2.06 A |
| 3,144,019 | 8/1964 | Haber ............................. | 128/2.06 A |
| 3,433,228 | 3/1969 | Keller, Jr. ....................... | 128/419 PG |
| 3,478,746 | 11/1969 | Greatbatch ..................... | 128/419 PG |
| 3,628,538 | 12/1971 | Vincent et al. .................. | 128/422 |
| 3,747,604 | 7/1973 | Berkovits ....................... | 128/419 PG |
| 3,815,611 | 6/1974 | Denniston ....................... | 128/419 D |

OTHER PUBLICATIONS

Bilqutay et al., "Journal of the American Medical Association", Vol. 191, No. 8, Feb. 22, 1965, pp. 649-653.

Schuder et al., "Transactions of the American Society for Artificial Internal Organs", Vol. XVI, 1970, pp. 207-212.

Primary Examiner—William E. Kamm
Attorney, Agent, or Firm—Lew Schwartz; Wayne Sivertson

[57] ABSTRACT

A device for preventing arrhythmias such as fibrillation in which a plurality of electrodes are placed at selected points on a heart to sense depolarizations. An astable multivibrator receives the depolarization signals from the electrodes and provides an output signal to a device which in turn provides cardiac stimulation signals to all of the electrodes on the heart for the purpose of preventing the arrhythmia. The multivibrator is preferably synchronized to the QRS complex of the heart with its refractory period. In a second embodiment of the device, separate sensing and stimulation electrodes are used.

15 Claims, 3 Drawing Figures

ARRHYTHMIA PREVENTION APPARATUS

BACKGROUND OF THE INVENTION

Arrhythmias of the heart, such as fibrillation, are well known to those familiar with the art. Localized or diffuse lesions of the myocardium, which may result from any one of various reasons, often lead to a pronounced dispersion of refractivity. As a result, under certain circumstances the heart does not experience a total, simultaneous depolarization, but rather there results an unequal repolarization which has a dispersed vulnerable phase. A depolarization excitation interspersed during this vulnerable phase finally leads to electrical fragmentation, and a consequential inception of ventricular fibrillation.

It is known that the proper application of an electrical shock to the heart can change a fibrillating heart back to synchronous action of all myocardial fibers, that is, the heart can be defibrillated. Defibrillation by electrical impulses to the heart is due to a regular development of propagation of electrical excitation by means of simultaneous switching of all myocardial fibers that have gone out of step to cause the arrhythmia. Many defibrillation devices are known in the prior art for providing a defibrillation pulse after the arrhythmia has commenced.

However, it has become apparent that electrical defibrillation is not an ideal means of therapy for arrhythmia problems. First of all, it is not immediately available in most cases, and even where implantable defibrillation devices are used, they provide stimulation signals only after the dangerous condition of arrhythmia already exists. Further, though implantable defibrillators were developed to eliminate existing ventricular fibrillation as rapidly as possible, they can do so only after detection of the actual state of fibrillation; and because of the high power requirements of the electrical shocks required to defibrillate, the operating time of such implantable defibrillators is highly limited. Further, even after detecting the advent of fibrillation, such prior art defibrillators require a discreet period of charge time before providing a defibrillation shock.

To overcome the problems discussed above, the apparatus of this invention was designed to prevent defibrillation by sensing heart depolarizations and providing cardiac stimulation level pulses to the heart to overcome electrical fragmentation before it causes defibrillation or other arrhythmias.

SUMMARY OF THE INVENTION

The apparatus of this invention provides a plurality of electrodes connected in spaced relation to a heart. A depolarization occurring at any point on the heart is first sensed by any one of the electrodes and then transmitted to a stimulation device which receives the signal from the electrode to supply stimulation pulses to the entire plurality of electrodes connected to the heart. By means of this technique of stimulation, an anti-fragmentation is achieved which has a counter-effect on ventricular fibrillation. The stimulation signal generator may be, for example, a synchronous demand cardiac pacer, but in any case will be a device synchronized to a normal depolarization of the heart such as the QRS complex.

DESCRIPTION OF THE INVENTION

Figure 1:
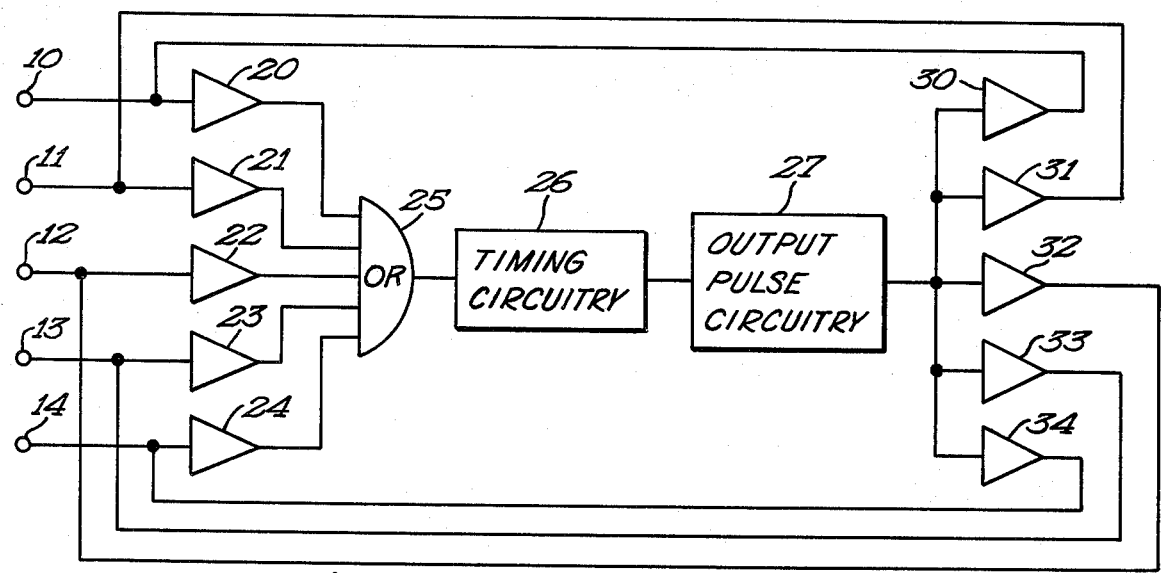
FIG. 1 is a block diagram of the first embodiment of the apparatus of this invention.

In FIG. 1, there is shown a first embodiment of the invention in which a plurality of terminals 10–14 are shown which are adapted to be connected to electrodes placed at various points on the heart (not shown), which electrodes act both as sensing and stimulation electrodes.

Terminals 10, 11, 12, 13 and 14 are connected, respectively, to a plurality of input signal amplifiers 20, 21, 22, 23 and 24. Input amplifiers 20–24 can be any one of a multiplicity of amplifiers well known to those skilled in the art, such as a single stage transistor amplifier.

The outputs of each of amplifiers 20–24 are connected to the inputs of a five stage OR gate 25. The output of gate 25 is connected to timing circuitry 26. The output of timing circuitry 26 is connected to output pulse circuitry 27. The output of pulse circuitry 27 is connected to each of the inputs of a plurality of output amplifiers 30–34. The outputs of amplifiers 30, 31, 32, 33 and 34 are connected, respectively, to terminals 10, 11, 12, 13 and 14.

In operation, when a depolarization signal appears at any one of terminals 10–14, such a signal having been sensed at the related electrode attached to the heart, it will be amplified by the respective of amplifiers 20–24 and presented to gate 25. The signal will pass through gate 25 into timing circuitry 26. Circuitry 26 is more fully described in the discussion of FIG. 2 below, however, to fully understand the operation of the circuitry of FIG. 1, it must be recognized that circuitry 26 will operate in the manner of an astable multivibrator having a predetermined operating frequency and refraction period. If an input signal at any of terminals 10–14 reaches circuitry 26 during the predetermined refractory period, there will be no output from circuitry 26 to output pulse circuitry 27. Circuitry 26 is synchronized to the normal QRS waves from the heart and will provide an output pulse when the QRS wave causes an input to circuitry 26. However, should a depolarization be sensed at any of the plurality of points on the heart at a time other than during the refractory period, this input to circuitry 26 will cause an output pulse to actuate output pulse circuitry 27.

Pulse circuitry 27, upon receiving an input signal, will provide an output stimulation pulse of predetermined width which will be amplified by each of amplifiers 30–34 to be felt on each of terminals 10–14, and thus be provided to all of the electrodes on the heart for stimulation purposes. Thus, an undesirable start of depolarization of an area of the myocardium will be sensed by any one or more of the electrodes and will result in a cardiac stimulation pulse to all of the electrodes. This cardiac stimulation will result in anti-fragmentation by capturing the entire heart comparatively quickly by bypassing the intraventricular interferences through the conductions that are under voltage. Therefore, the input dispersion of refractivity is reduced, the vulnerable phase becomes narrower, and in this manner fibrillation is counter-effected in its nascent state.

Figure 2:
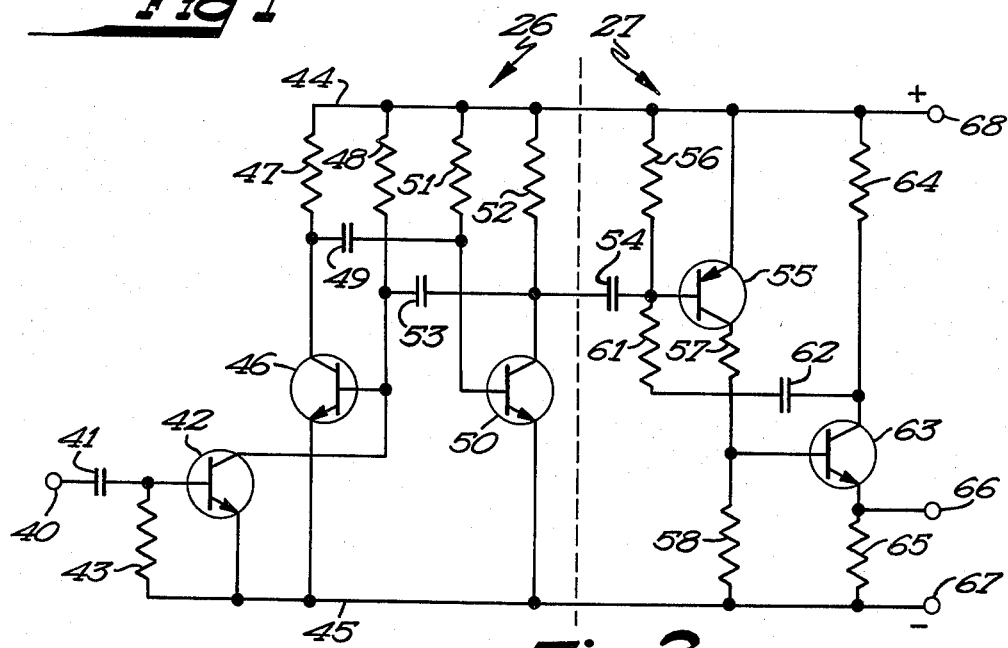
FIG. 2 is a schematic diagram of portions of the diagram of FIG. 1.

Referring now to FIG. 2, there are shown schematic diagrams of blocks 26 and 27 of FIG. 1. Timing circuitry 26 is shown to the left of the vertical dashed line of FIG. 2, while output circuitry 27 is shown to the right of the dashed line.

In FIG. 2 there is shown an input terminal 40 which is adapted to be connected to the output of gate 25 of FIG. 1. Terminal 40 is connected through a capacitor 41 to the base of a transistor 42. The base of transistor 42 is also connected through a resistor 43 to a negative bus line 45. The emitter of transistor 42 is also connected to bus 45. The collector of transistor 42 is connected to the base of a transistor 46, and through a resistor 48 to a positive bus line 44. The emitter of transistor 46 is connected to negative bus 45, and the collector of transistor 46 is connected through a resistor 47 to bus 44. The collector of transistor 46 is also connected through a capacitor 49 to the base of a transistor 50, and through a resistor 51 to bus 44. The emitter of transistor 50 is connected to bus 45. The collector of transistor 50 is connected through a resistor 52 to bus 44, through a capacitor 53 to the base of transistor 46, and through a capacitor 54 to the base of a transistor 55. The emitter of transistor 55 is connected to bus 44. The base of transistor 55 is connected through a resistor 56 to bus 44. The collector of transistor 55 is connected through a serial combination of a resistor 57 and a resistor 58 to bus 45. The base of transistor 55 is also connected through the serial combination of a resistor 61 and a capacitor 62 to the collector of a transistor 63. The base of transistor 63 is connected to a junction between resistors 57 and 58. The collector of transistor 63 is also connected through a resistor 64 to bus 44. The emitter of transistor 63 is connected through a resistor 65 to bus 45, and is connected to an output terminal 66. Terminal 66 is adapted to be connected to amplifiers 30–34 of FIG. 3. Negative bus line 45 is connected to a negative power input terminal 67, and positive bus line 44 is connected to a positive voltage input terminal 68.

In operation, QRS signals and depolarization signals appearing at terminals 10–14 of FIG. 1 will pass through amplifiers 20–24 and gate 25 to appear at terminal 40 of FIG. 2. This input signal will be felt on the base of transistor 42 to turn it on and switch transistor 46 to cut-off. Transistors 46 and 50, and their associated components, comprise an astable multivibrator. The output at the collector of transistor 50 is an asymmetrical square pulse, composed of, in the preferred embodiment, an 840 millisecond off or high portion, and a 160 millisecond on or low portion. If a pulse appears at the base of transistor 42, due to an input signal during the 840 millisecond off interval, transistor 46 will be switched to cut-off. As the collector of transistor 46 rises, transistor 50 will saturate due to the charge transferred to its base through capacitor 49. Thus, input pulses falling during the 840 millisecond off interval will shorten this off interval, and thereby increase the operation frequency of the astable multivibrator. The 160 millisecond on interval is referred to as the refractory period.

The trailing edge of the pulse appearing at the collector of transistor 50 will be felt through capacitor 54 on the base of transistor 55. Transistors 55 and 63 comprise a well-known monostable multivibrator, in conjunction with their associated components, which operates in a manner well known to those skilled in the art, to provide an output at terminal 66 for a predetermined pulse duration. Terminal 66 is connected to the inputs of amplifiers 30–34 of FIG. 1, and thus the trailing edge of the pulse appearing at the collector of transistor 50 will cause stimulation pulses to appear through all of the terminals 10–14 to all of the electrodes connected in spaced relation on the heart.

Timing circuitry 26 can be likened to an R-wave synchronized pulse generator. That is, it has a predetermined operating frequency with a predetermined refractory period. Pulses falling outside the refractory period will shorten the operation frequency of the circuitry, and result in an output stimulation pulse. Pulses falling during the refractory period will not result in stimulation pulses to the heart. By synchronizing the output pulses to the QRS complex, through proper selection of the operation frequency and refractory period, undesirable side effects of rhythmical stimulations are avoided. The 1 Hz operation frequency chosen for the above described embodiment is only an example, but is preferred because, with a 160 millisecond refractory period, it allows synchronization to a maximum rate of 375 pulses per minute.

Figure 3:
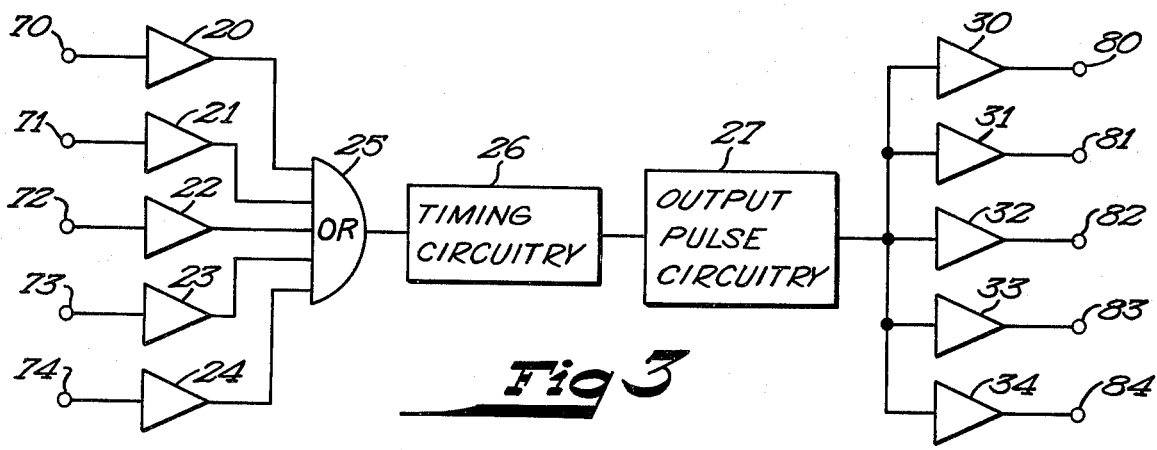
FIG. 3 is a block diagram of a second embodiment of the apparatus of this invention.

Referring now to FIG. 3, there is shown a second embodiment of the apparatus of this invention in which separate leads are used for sensing heart depolarizations and for stimulating the heart. Again in FIG. 3, the well known electrodes are not shown but terminals adapted to be connected to the electrodes are depicted.

A plurality of terminals 70–74 are shown and are adapted to be connected to a plurality of sensing electrodes placed in space relation on the heart. Terminals 70, 71, 72, 73 and 74 are connected, respectively, to amplifiers 20–24. Amplifiers 20–24 are again connected through gate 25 to circuitry 26, which is in turn connected to circuitry 27. The output of circuitry 27 is connected to the inputs of amplifiers 30–34. In FIG. 3 the outputs of amplifers 30–34 are connected to, respectively, terminals 80, 81, 82, 83 and 84. In the embodiment of FIG. 3, terminals 80–84 are adapted to be connected to a second plurality of electrodes connected in spaced relation on the heart for purposes of providing stimulation signals to the heart.

The operation of the apparatus of FIG. 3 is exactly the same as that described above for FIGS. 1, and 2, with the single exception that the stimulation signals are provided to separate electrodes from the electrodes which perform the sensing function.

From the above description of the apparatus of this invention, it will be apparent that there may be other embodiments other than the preferred embodiments shown which are capaable of performing the fibrillation prevention function of this invention, but which will still be within the scope of this invention. It should also be noted that the fibrillation prevention apparatus of this invention has been tested clinically on animals and has been shown to be an effective means of preventing the arrythmia.

What is claimed is:

1. Cardiac electrical stimulation apparatus comprising: first means for sensing depolarization at any one of a plurality of areas on a heart; second means for providing cardiac stimulation signals to a plurality of areas on the heart in rapid response to any sensed depolarization by the first means; and means connecting the first means to the second means.

2. The apparatus of claim 1 in which: the first means includes multivibrator means having a predetermined refractory period; and the second means includes means for limiting stimulation pulses to a duration shorter than said refractory period and occurring during said refractory period.

3. The apparatus of claim 2 in which the multivibrator means include means for setting said refractory period at a time value which allows synchronization of the stimulation signals with cardiac QRS signals.

4. Fibrillation prevention apparatus comprising: a plurality of electrode means adapted to be connected in spaced relation on a heart; means for responding rapidly to a signal from any one of the electrode means to provide cardiac stimulation signals to all the electrode means; and means connecting the electrode means to the means for responding.

5. The apparatus of claim 4 in which: the means for responding includes means for synchronizing the stimulation signals to the cardiac QRS signals.

6. Fibrillation prevention apparatus comprising: a plurality of sensing electrode means adapted to be connected in spaced relation on a heart; a plurality of stimulation electrode means adapted to be connected in spaced relation on the heart; means for responding rapidly to a signal from any one of the sensing electrode means to provide stimulation signals on all of the stimulation electrodes; and means connecting the means for responding to the sensing electrodes and the stimulation electrodes.

7. The apparatus of claim 6 in which: the means for responding includes means for synchronizing the stimulation signals to the cardiac QRS signals.

8. Fibrillation prevention apparatus comprising: a plurality of electrode means adapted to be connected in spaced relation on a heart; input means connected to the electrode means; output means connected to the electrode means; the input means including means for responding to signals from any of the electrode means to provide a signal; astable multivibrator means having a preset refractory period and an operation frequency which is variable in response to signals from the input means; means connecting the multivibrator means between the input means and the output means; and the output means including means for responding to the multivibrator means to provide heart stimulation signals to all the electrode means the heart stimulating signal occuring quickly after an input signal to said multivibrator means.

9. Fibrillation prevention apparatus comprising: a plurality of sensing electrodes adapted to be connected in spaced relation on a heart; input means connected to the sensing electrode means; a plurality of stimulation electrodes adapted to be connected in spaced relation on the heart; output means connected to the stimulation electrode means; the input means including means for responding to signals from any of the sensing electrode means to provide a signal; astable multivibrator means having a preset refractory period and an operation frequency variable in response to signals from the input means; means connecting the multivibrator means between the input means and the output means; means in the multivibrator means responsive to the input means signal to provide another signal; and the output means including means for responding to the multivibrator means signal to provide heart stimulation signals to all the stimulation electrode means, the heart stimulating signal occuring quickly after an input signal to said multivibrator means.

10. Fibrillation prevention apparatus comprising: a plurality of electrodes adapted to be connected in spaced relation on a heart; amplifier means connected to the electrodes; multivibrator means connected to the amplifier means and responsive to a signal from any one of the electrodes to provide an output signal; and output amplifier means connected to the multivibrator means and the electrodes, and responsive to an output signal to provide heart stimulation signals simultaneously to all the electrodes the heart stimulating signal occuring quickly after an input signal to said multivibrator means.

11. The apparatus of claim 10 in which: the multivibrator means has a refractory period longer than the duration of the stimulation signals.

12. Fibrillation prevention apparatus comprising: a plurality of sense electrodes adapted to be connected in spaced relation on a heart; a plurality of stimulation electrodes adapted to be connected in spaced relation on a heart; amplifier means connected to the sense electrodes; multivibrator means connected to the amplifier means and responsive to a signal from any one of the sense electrodes to provide an output signal; and output amplifier means connected to the multivibrator means and the stimulation electrodes, and responsive to an output signal to provide stimulation signals simultaneously to all the stimulation electrodes the heart stimulating signal occuring quickly after an input signal to said multivibrator means.

13. The apparatus of claim 12 in which: the multivibrator means has a refractory period longer than the duration of the stimulation pulses.

14. Cardiac arrhythmia prevention apparatus comprising: a plurality of electrodes adapted to be connected to a heart; an R-wave synchronous pulse generator having input means and output means; the generator input means and output means connected to the electrodes; and the generator including means for providing cardiac stimulation pulses to all the electrodes in rapid response to a signal from at least one of the electrodes.

15. Cardiac arrhythmia prevention apparatus comprising: a plurality of sense electrodes adapted to be connected to a heart; a plurality of stimulation electrodes adapted to be connected to a heart; an R-wave synchronous pulse generator having input means and output means; the generator input means connected to the sense electrodes and the generator output means connected to the stimulation electrodes; and the generator including means for providing cardiac stimulation pulses to all the stimulation electrodes in rapid response to a signal from at least one of the sense electrodes.

* * * * *